United States Patent
Eiger (10) Patent No.: US 10,806,937 B2
(45) Date of Patent: Oct. 20, 2020

(54) HEAT DISPERSION FOR IMPLANTABLE MEDICAL DEVICES

(71) Applicant: Nuvectra Corporation, Plano, TX (US)

(72) Inventor: Jay H. Eiger, Eastlake, OH (US)

(73) Assignee: CIRTEC MEDICAL CORP., Brooklyn Park, MN (US)

( * ) Notice: Subject to any disclaimer, the term of this patent is extended or adjusted under 35 U.S.C. 154(b) by 233 days.

(21) Appl. No.: 15/985,179

(22) Filed: May 21, 2018

(65) Prior Publication Data

US 2018/0264275 A1    Sep. 20, 2018

Related U.S. Application Data

(63) Continuation of application No. 13/359,739, filed on Jan. 27, 2012, now Pat. No. 9,981,137.

(51) Int. Cl.
*A61N 1/378* (2006.01)
*A61N 1/37* (2006.01)

(52) U.S. Cl.
CPC ............ *A61N 1/3787* (2013.01); *A61N 1/37* (2013.01)

(58) Field of Classification Search
CPC ................................ A61N 1/37; A61N 1/3787
See application file for complete search history.

(56) References Cited

U.S. PATENT DOCUMENTS

| | | | |
|---|---|---|---|
| 3,920,175 A | 11/1975 | Hamilton et al. | |
| 4,250,727 A | 2/1981 | Baril et al. | |
| 4,294,419 A | 10/1981 | Fouse et al. | |
| 4,350,155 A | 9/1982 | Thompson | |
| 4,951,491 A | 8/1990 | Lorenz | |
| 5,336,246 A | 8/1994 | Dantanarayana | |
| 5,823,034 A | 10/1998 | Nelepovitz | |
| 5,843,142 A | 12/1998 | Sultan | |
| 5,863,467 A | 1/1999 | Mariner et al. | |
| 5,991,665 A | 11/1999 | Wang et al. | |
| 6,029,269 A | 2/2000 | El-Soudani | |
| 6,033,506 A | 3/2000 | Klett | |
| 6,038,475 A | 3/2000 | Sikorski et al. | |
| 6,116,070 A | 9/2000 | Oshida et al. | |
| 6,131,651 A | 10/2000 | Richey, III | |
| 6,287,118 B1 | 9/2001 | Naganuma et al. | |
| 6,300,150 B1 * | 10/2001 | Venkatasubramanian | ................... B82Y 10/00 257/470 |

(Continued)

FOREIGN PATENT DOCUMENTS

WO    WO200102632    1/2001

*Primary Examiner* — Christopher A Flory
(74) *Attorney, Agent, or Firm* — Haynes and Boone, LLP (57) ABSTRACT

An implantable medical device that includes electrical circuitry for providing a therapy to a patient. The device also includes a housing forming an inner chamber that is adapted for receiving, at least a portion of the electrical circuitry. The device further includes a thermally conductive material that is configured to disperse heat from a first portion of the implantable medical device that is located in proximity to a heat generating component of the electrical circuitry, to a second portion of the implantable medical device that is not located in proximity to said heat generating component. The thermally conductive material is a discrete component separate from the electrical circuitry and the housing.

20 Claims, 9 Drawing Sheets

(56) References Cited

U.S. PATENT DOCUMENTS

| | | |
|---|---|---|
| 6,313,031 B1 | 11/2001 | Schuele et al. |
| 6,432,142 B1 | 8/2002 | Kamiya et al. |
| 6,517,534 B1 | 2/2003 | McGovern et al. |
| 6,550,124 B2 | 4/2003 | Krajewski et al. |
| 6,655,575 B2 | 12/2003 | Mishra |
| 6,660,116 B2 | 12/2003 | Wolf et al. |
| 6,694,790 B2 | 2/2004 | Ryntz et al. |
| 6,776,214 B2 | 8/2004 | Ray et al. |
| 6,888,715 B2 | 5/2005 | Stevenson et al. |
| 7,164,077 B2 * | 1/2007 | Venkatasubramanian ............ B01L 7/52 136/203 |
| 7,225,032 B2 | 5/2007 | Schmeling et al. |
| 7,232,625 B2 | 6/2007 | Leysieffer et al. |
| 7,261,782 B2 | 8/2007 | Hwang et al. |
| 7,351,240 B2 | 4/2008 | Hassler, Jr. et al. |
| 7,494,488 B2 | 2/2009 | Weber |
| 7,499,260 B2 | 3/2009 | Schott et al. |
| 7,533,794 B2 | 5/2009 | Comley et al. |
| 7,713,651 B2 | 5/2010 | Leysieffer et al. |
| 7,848,817 B2 | 12/2010 | Janzig et al. |
| 7,901,509 B2 | 3/2011 | Mariner et al. |
| 8,066,712 B2 | 11/2011 | Truckai et al. |
| 8,180,453 B2 | 5/2012 | Greenberg et al. |
| 8,260,435 B2 | 9/2012 | Johnson et al. |
| 8,267,983 B2 | 9/2012 | Rogers et al. |
| 8,339,769 B2 | 12/2012 | Schott et al. |
| 8,380,302 B2 | 2/2013 | Schmalhurst et al. |
| 8,430,887 B2 | 4/2013 | Truckai et al. |
| 8,437,865 B2 | 5/2013 | Dabney et al. |
| 9,630,231 B2 | 4/2017 | Kelsch et al. |
| 2003/0047253 A1 | 3/2003 | Robinson et al. |
| 2003/0097178 A1 | 5/2003 | Roberson et al. |
| 2005/0075694 A1* | 4/2005 | Schmeling ............ A61N 1/3787 607/61 |
| 2006/0086118 A1* | 4/2006 | Venkatasubramanian ............ F25B 21/02 62/259.2 |
| 2006/0289050 A1* | 12/2006 | Alley ............... H01L 35/34 136/203 |
| 2006/0289052 A1* | 12/2006 | O'Quinn ............ H01L 35/08 136/230 |
| 2007/0089773 A1* | 4/2007 | Koester ............ H01L 35/34 136/230 |
| 2008/0103556 A1 | 5/2008 | Li et al. |
| 2008/0168775 A1 | 7/2008 | Windheim et al. |
| 2008/0264464 A1 | 10/2008 | Lee et al. |
| 2008/0294207 A1 | 11/2008 | Kast et al. |
| 2010/0256709 A1 | 10/2010 | Kallmyer |
| 2011/0009773 A1 | 1/2011 | Hower et al. |
| 2011/0295347 A1 | 12/2011 | Wells et al. |
| 2012/0299175 A1 | 11/2012 | Tran |
| 2012/0310313 A1 | 12/2012 | Rogers et al. |
| 2013/0078149 A1 | 3/2013 | Holmes et al. |

* cited by examiner

HEAT DISPERSION FOR IMPLANTABLE MEDICAL DEVICES

CROSS-REFERENCE TO RELATED APPLICATIONS

This application is a continuation of U.S. Nonprovisional patent application Ser. No. 13/359,739, filed on Jan. 27, 2012, the disclosure of which is incorporated herein in its entirety and for all applicable purposes.

BACKGROUND OF THE INVENTION

Field of the Invention

This application relates generally to electrically powered implantable medical devices and the dispersion of heat generated by electrical componentry within the devices and/or magnetic fields used for inductively recharging a power source of the implant.

In the field of implantable medical devices (IMD), electrical componentry is used to monitor the patient, disperse medications, and also to apply therapeutic electrical stimulation to tissue. These IMDs often have power requirements in excess of what can be provided by conventional batteries, thus rechargeable batteries are provided. To prevent the need for electrical wiring to protrude from a patient's skin, which presents an infection hazard, most implant rechargeable batteries are charged via an inductive field provided by an external charger to an implant charge receiving system included in the IMD. This implant charge receiving system allows the rechargeable battery of the IMD to be recharged through the patient's skin without physical contact between the implant and the external charging unit. In addition, some IMDs are continuously externally powered by inductive power fields provided by an external power unit, much like the external charger that is affixed to the patient whenever the device is used. These implants often do not include a rechargeable battery for powering the device. Cochlear devices in particular are often powered in this manner.

However, in both type of IMDs, with or without rechargeable batteries, inductive power fields are required to power the electrical componentry. Electrically driven implantable devices are used, for example, as neuro-stimulators including pain suppression, hearing aids (e.g. cochlear devices), cardiac pacemakers, and defibrillators. However, they may also be used for drug infusion and dispensing systems, nerve and bone growth stimulators, digestive track stimulators, artificial vision apparatus, artificial organs including artificial hearts, bladder stimulators, and for the purposes of implanted sensors that monitor but do not actively stimulate tissue. Additionally, IMDs have been used as combinations of the above listed devices, such as a combined cardiac pacemaker and cardiac defibrillator. Thus, the electrical componentry may provide therapeutic electrical stimulation of tissue, monitoring of the patient, medication dispensing, and other medical purposes. Further, the electrical componentry may also include circuitry for monitoring the IMD itself and for communicating with external programmers, device controllers, and patient information gathering systems.

As a result of the proliferation of electrically powered IMDs into new areas of medical treatment, electronic components have been upgraded and perform ever more complicated monitoring/diagnosis and therapeutic electrical stimulation using smaller electrical circuitry while rechargeable batteries have increased in life span and energy density and decreased their recharging times. However, despite all of the improvements in electrically powered IMDs since the invention of the original pacemaker in the late 1950s, transdermal inductive powering, for charging of rechargeable batteries or direct powering of an implant, is now the medical standard for powering of many implants. However, despite the fact that new rechargeable battery technologies allow for fast recharging of implanted batteries, for example newer lithium ion chemistries may be recharged in an hour, whereas IMDs often require longer charging times. These longer charging times are necessitated, not by battery chemistries that prevent fast recharges, but due to the heat generated during transdermal inductive charging or powering of the device. For example, an inductive power field, from an external charger, may cause substantial eddy currents on the housing of the implant, which cause significant heat to build up in the implant. Furthermore, substantial heat is generated by the recharging circuitry in the implant during the process of converting the inductive power field into a useable current for the rest of the electrical circuitry engaged in, for example therapeutic electrical stimulus, patient monitoring, battery charging, and telemetry with external devices. Thus, heat generation increases recharging times for electrically powered implants, inconveniencing patients. One method proposed for reducing charging times is to include a fan with the external charger, U.S. Pat. No. 5,991,665 to Wang et al. However, this solution primarily cools the skin and does not increase the circulation of fluids within the body that come in contact with the implant's housing, which is used as a heat sink.

Additionally, heat generating electrical circuitry, in particular recharging circuitry, is usually located in limited portions of the implantable device causing hotspots on areas of the implant housing located near the heat generating componentry. Excessive heating on the housing external surfaces may cause necrosis (tissue death) in the areas exposed to the hotspots. Accordingly, industry standards allow the external portion of the implant housing, that is exposed to the patient's tissue, to be only 3 degrees higher in Celsius temperature than the surrounding tissue, which is about 37 degrees Celsius. Thus, inductive power fields currently must be lowered to reduce temperatures which results in an increase in charging times. There is a need for a way to evenly disperse heat generated in electrically powered IMDs over the entire housing to prevent hotspots. This effectively increases the usable surface area of the heat sink, which is the external portion of the implant housing. Thus, dispersing heat throughout the implant housing would allow for the use of stronger inductive power fields which decreases recharging times and/or increases the amount of power supplied to implant.

SUMMARY OF THE INVENTION

Provided are a plurality of embodiments the invention, including, but not limited to, a device for heat transfer within an implantable medical device. The device includes electrical circuitry that connects to a therapeutic electrical lead for providing electrical stimulation to a patient. The device also includes a housing forming an inner chamber that is adapted for receiving, at least, a portion of the electrical circuitry and the therapeutic electrical lead is external to the housing. The device further includes a thermally conductive material that is configured to disperse heat from a first portion of the implantable medical device that is located in proximity to a heat generating component of the electrical circuitry, to a second portion of the implantable medical device that is not located in proximity to said heat generating component.

Also provided is a method for providing a therapy with an implantable medical device. The method optionally includes implanting the implantable medical device including an electrical componentry into a patient. At least some of the electrical componentry is associated with the method is located inside a housing of the implantable medical device. The method further includes providing a therapeutic operation with the electrical componentry. The therapeutic operation may include providing an electrical stimulus to a patient and the tissue of the patient or reading electrical signals of the tissue, temperature signals, sensing motion, or taking other readings with the electrical circuitry. The method further includes generating heat with the electrical componentry which may be generated during the inductive recharging of the power supply of the implantable medical device, rapidly discharging the battery during an emergency, providing a therapy, or any other reason that the implant may be causing heating due to operations by the electrical circuitry.

Still further provided is a method for transferring heat in an implantable medical device including, providing a therapeutic operation with the implantable medical device. The method may further include generating heat with a component of the implant and dispersing heat generated by the component with a thermally conductive material from a first portion of the implantable medical device located in proximity to said heat generating component to a second portion of the implantable medical device that is not located in proximity to said generated heat of the component.

Also provided are additional embodiments of the invention, some, but not all of which, are described herein below in more detail.

BRIEF DESCRIPTION OF THE DRAWINGS

The features and advantages of the examples of the present invention described herein will become apparent to those skilled in the art to which the present invention relates upon reading the following description, with reference to the accompanying drawings, in which.

DETAILED DESCRIPTION OF THE EXAMPLE EMBODIMENTS

Figure 1:
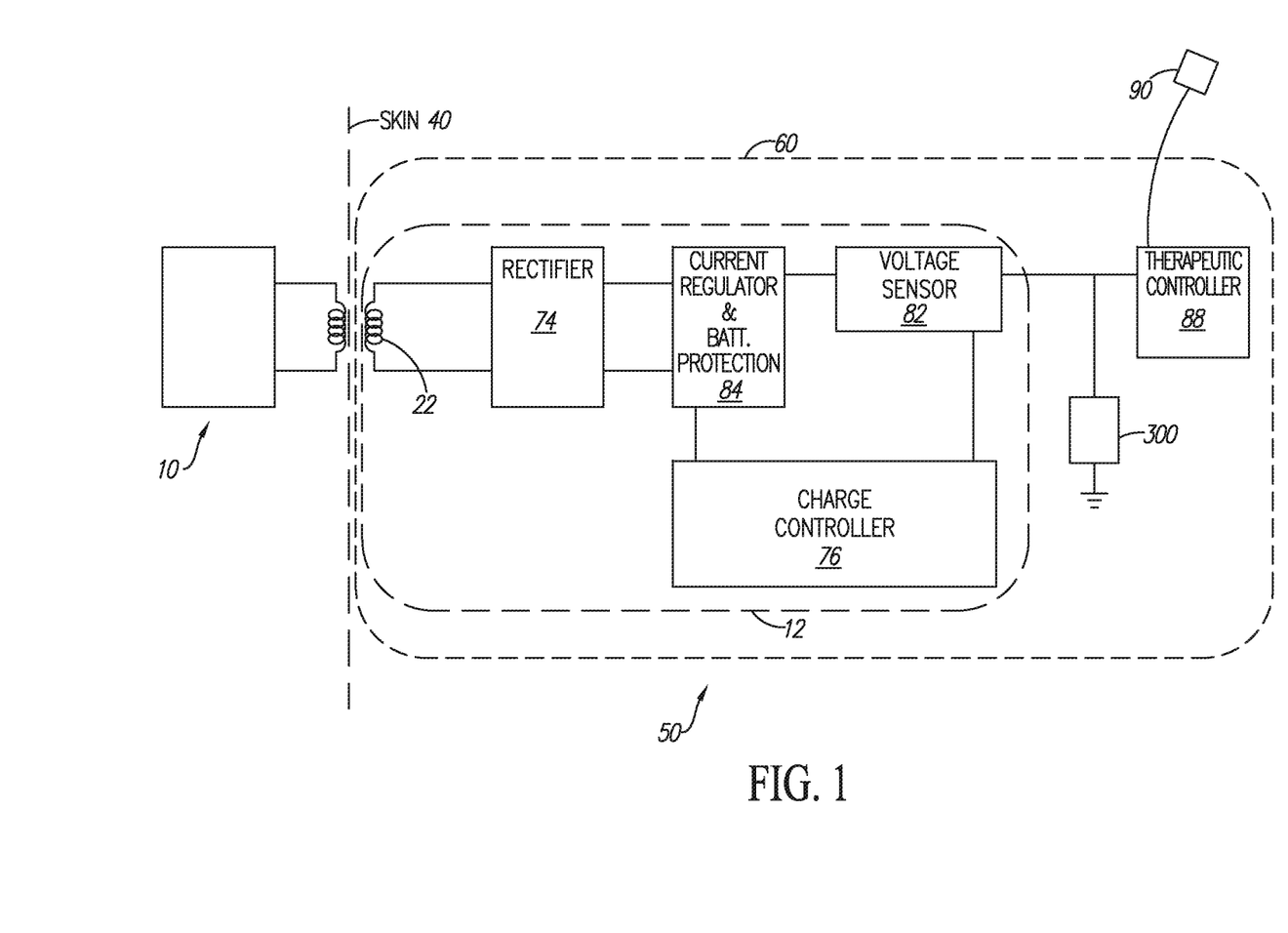
FIG. 1 shows a brief schematic of an example electrically powered implantable medical device with an inductively coupled external charger.

Example implantable medical devices (IMDs) 50 include a device for heat transfer and are shown in FIG. 1. The IMD 50 includes electrical circuitry with a connection to a therapeutic electrical lead 90 for providing electrical stimulation to a patient. The electrical circuitry may include, for example, recharging circuitry 12, a therapeutic controller 88 for providing electrical stimulus to the therapeutic electrical lead 90. The IMD 50 also includes a housing 60 forming an inner chamber that is adapted for receiving, at least, a portion of the electrical circuitry. In one embodiment, the therapeutic electrical lead 90 is external to the housing, in other embodiments other portions of the electronic circuitry are external to the housing. For example, the housing may consist of two housings and the battery. A portion of the electronic circuitry may be exterior to the housing and may be contained in a separate housing.

Figure 2:
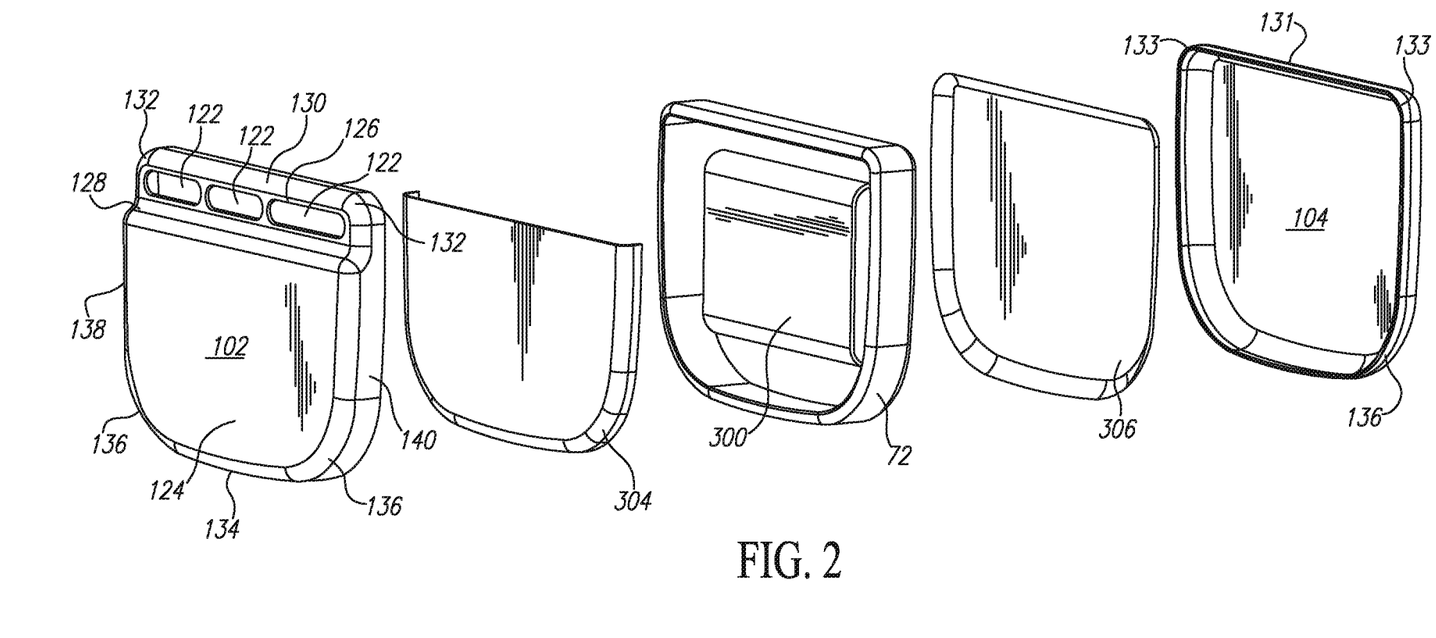
FIG. 2 shows the major physical components of an example implantable medical device.

The IMD 50 also includes a thermally conductive material (shown in FIG. 2) that is configured to disperse heat from a first portion of the IMD 50 that is located in proximity to a heat generating component of the electrical circuitry (e.g. the charge coil of FIG. 2), to a second portion of the IMD 50 that is not located in proximity to said heat generating component. For example, the thermally conductive material may be located within a wall of the housing as an integrated housing component or it may be located on the exterior of the housing as a coating between the housing and a tissue that surrounds the implantable medical device. Additionally, the thermally conductive material may be located within the inner chamber of the housing between the housing and the heat generating component of the electrical circuitry as depicted in FIG. 2. The thermally conductive material may be optionally located within the inner chamber, disposed between the housing and the electrical circuitry. The thermally conductive material may be a sheet that is form fitted to, at least, a portion of the inner chamber with the electrical circuitry contacting it. In this configuration, heat would be transferred from the electrical circuitry to the sheet and then to the housing.

FIG. 2 gives a detailed depiction of the sheet thermally conductive material located within the housing interior and the interior of the housing, the inner chamber of housing 60 may be formed by the two portions of the housing 102 and 104 of FIG. 2. The inner chamber may contain thermally conductive material. The thermally conductive material may be thermally conductive material sheets 304, 306 that act as heat spreaders for the implant charge coil 72, the recharging circuitry 12 of FIG. 1, and battery 300. Housing portions 102 and 104 may be welded together to form a hermetically sealed inner chamber that contains the electrical circuitry. Optional embodiments may include housings with multiple inner chambers for segregating internal components. For example, the charge coil 72 may be in a separate chamber from the other circuitry for the purpose of shielding the other circuitry from the inductive power signal used to recharge the implant's battery 300.

FIG. 2 is a partial exploded view of an implantable medical device and specifically depicts the housing portions and components housed within the housing portions. The battery 300 and a controller, which can include an application specific integrated circuit, are located within the housing portions 102, 104 which form an inner chamber of the housing (see housing 60 of FIG. 1). An implant charging coil 72 is also located within the housing portions 102, 104. The implant charging coil 72 charges the battery via electromagnetic energy supplied by a non-contact external charger 10 located outside of the body. Heat spreader sheets 304, 306 draw heat from the coil 72 and other electronic circuitry (e.g. recharging circuitry 12 of FIG. 1) away from the peripheral portions of the housing portions 102, 104, toward more central portions of the housing, to help reduce the formation of hot spots along the housings.

The heat spreader sheets 304, 306 can be formed from a graphite sheet material or other suitably heat conductive materials, and generally conform to the interior contours of the housing portions 102, 104. The thermally conductive material may be in a sheet form and may include heat spreader sheets 304 and 306 that are configured to disperse heat from a first portion of the housing portions 102 & 104 (housing 60 of FIG. 1) that is located in proximity to a heat generating component of the electrical circuitry (e.g. implant charge coil 72, recharging circuitry 12). Thus, the heat spreaders 304, 306 may prevent hotspots by evenly distributing heat generated within the implant over the entire implantable device surface. The utilization of the greatest possible surface area of the implant for cooling allows for higher power electrical applications to be performed, including faster recharging of the implant battery.

It can be seen in FIG. 2 that the front housing 102 includes a deep portion 124 and a shallow portion 126. A transition portion 128 joins the deep portion 124 and the shallow portion 126. The deep portion 124 is suitable for housing various parts of the pulse generation circuitry, such as the battery. The shallow portion 126 includes the feed through holes 122. The feed through pins 120 (FIGS. 1 and 2) are aligned with the feed through holes, as discussed above. The feed through holes 122 can be cut or punched into the shallow portion 126, after the front housing portion 102 is formed, as discussed below. The transition portion 128 can provide a shelf onto which the header 108 (FIGS. 1 and 2) is adhered.

Both the front housing portion 102 and the rear housing portion 104 have a first edge portion 130. The first edge portions 130 are shown as being substantially straight (e.g., extends along a substantially straight line). Alternatively, the first edge portions can be curved. The first edge portions 130 extend between respective first sets of rounded corners 132 on the front and rear housing portions 102, 104. The header 108 (FIGS. 1 and 2) can be adhered to one or both of the first edge portions 130.

Figure 3A:
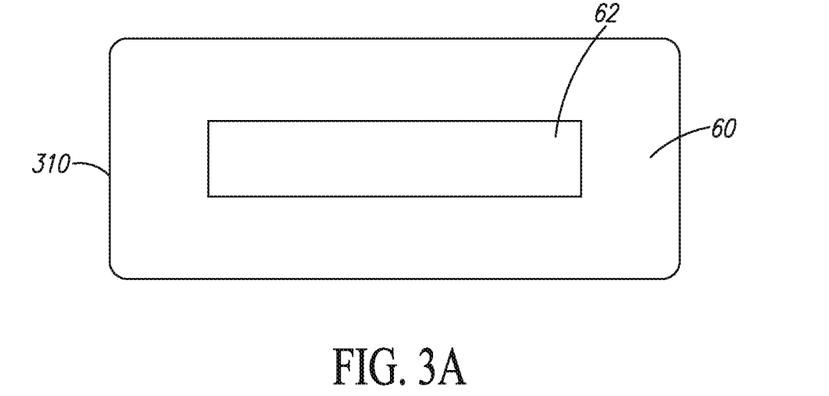
FIG. 3A shows an example implant housing with an external coating for heat distribution.
Figure 3B:
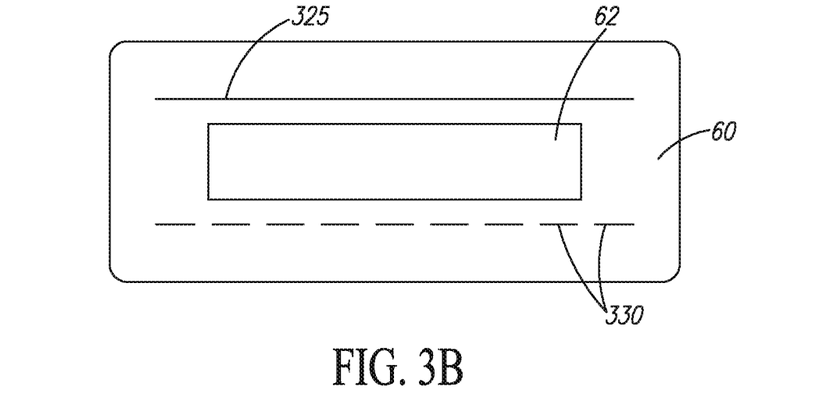
FIG. 3B shows an example implant housing with an integrating heat distribution sheeting.

In another embodiment, the IMD 50 includes the thermally conductive material being applied to the exterior of the housing. The material may be a coating material 310 applied to the exterior of the housing 60, as depicted in FIG. 3A. Alternatively, the coating may be applied to the inner chamber 62 of the housing 60. The thermally conductive material may be configured to disperse heat from the first portion of the housing that is located in proximity to a heat generating component of the electrical circuitry, to a tissue of a patient in proximity to the second portion of the housing that is not located in proximity to said heat generating component. In still another embodiment, shown in FIG. 3B, the thermally conductive material is implanted, placed within, or formed within the housing. The thermally conductive material may be a sheet layer 325, multiple strips 330, or multiple overlapping strips, within the housing 60.

In one particular embodiment, thermally conductive materials may include pyrolytic graphite, the finest forms of which are often called Highly Ordered Pyrolytic Graphite (HOPG) which is manufactured through a pyrolysis reaction. In this reaction, hydrocarbon gas is decomposed at 3300 K in a vacuum. The carbon atoms form again into a structure that in one direction consists of planar layers of hexagonally arranged carbon atoms the a-b layer, and in the other perpendicular direction consists of randomly oriented atoms (c direction). For example, the a-b layer may be associated with the x-y plane while the c layer may be associated with the z-plane. This manufacturing method gives an almost perfect lattice in the layers described, whereas natural graphite always has defects in its crystal structure with regards to the layers or planes.

The highly anisotropic lattice structure, with a strong atomic binding in the planar layers (a-b) and a weak atomic binding in the perpendicular direction (c layer), gives pyrolytic graphite its extraordinary heat transferring properties. For example, the thermal conductivity in the direction of the planar layers is one of the highest, but in the other direction it is lower than that of alumina. Also the mechanical strength, electrical conductivity, magnetic properties, and thermal expansion reflect this anisotropy. The degree of anisotropy depends on how parallel the planar layers are. This is characterized by a term called mosaic spread angle, and as the number becomes smaller, it gives a higher parallelism and thus a more perfect lattice. HOPG may have thermal conductivities in the range of 400-1700 W/m-K in the a-b layer while having a thermal conductivity of only 3.5 W/m-K in the c layer. Thus, HOPG has excellent properties for spreading heat over an area, and thus very thin layers of the material may be used for heat spreading.

The thermally conductive materials may also be describes more generally as "Thermal pyrolytic graphite" (TPG), which is a pyrolytic graphite and more particularly an annealed pyrolytic graphite. TPG is alternatively known as compressed annealed pyrolytic graphite (CAPG). These different graphite materials are commercially manufactured and available from General Electric Company. Conventional high conductivity graphite reinforced composites have in-plane thermal conductivity on the order of 300 W/m-k. However, TPG (and CAPG) can provide conductivities well over 1500 W/m-k. For the purpose of this invention, CAPG and TPG may be used interchangeably. For further description of this material see U.S. Pat. No. 6,131,651 to Richey and U.S. Pat. No. 5,863,467 to Mariner et al.

Although TPG has a high thermal conductivity in the one plane, for example the x-y plane (also known as the a-b direction), its thermal conductivity in a direction normal to that plane (perpendicular) or the z-plane (also known as the c direction) is low. For example, in one embodiment, TPG has a z-plane directional thermal conductivity of less than 20 W/m-K. TPG, therefore, rapidly spreads heat in the x-y plane but resists heat flow in the z-plane. This makes TGP ideal for heat spreading applications.

In one embodiment, the thermally conductive material sheet of TGP is disposed between heat generating electrical components and the housing may be a sheet in the x-y plane (with high thermal conductivity). The TGP sheet may be applied to the interior wall of the inner chamber of the implant housing with the z-plane contacting or substantially contacting (e.g. with a layer between) a wall of the inner chamber of the implant. Thus, the sheet easily spreads heat over the sheet's surface in the x-y plane before being transferred in the z-plane to the wall of the housing.

In another embodiment, the thermally conductive material is a sheet having in plane thermal conductivity greater than 1000 W/m-K, an out of plane thermal conductivity of less than 10 W/m-K, and a thickness between 1 micron and 2 mm. In another embodiment, thermally conductive material is composed of sheet and include a thermally conductive pyrolytic graphite, which includes HOPG, with an in plane thermal conductivity of greater than 1000 W/mK and an out of plane thermal conductivity of less than 10 W/m-K.

TPG is a material that is commercially available in a sheet format of 1 micron to 2 mm thickness from General Electric. Very thin layers of TGP may be used for transferring heat. TGP sheets may be analogous to the "thermally conductive material sheet" described in the claims. Additionally, TGP may also include an adhesive layer on one side of the sheet (in the x-y plane) and an electrically insulating layer on the other side of the sheet. In the embodiment where the thermally conductive material is disposed between the housing and the electrical componentry, this configuration of TGP allows the sheet to be affixed to the housing with the adhesive while having the electrical circuitry contacting the sheet's insulated side for maximum heat transfer and prevention of short circuits.

In one embodiment, TGP may be applied to the external surface of an implant's housing. Electrical componentry may transfer heat to the housing, causing hotspots, and then the housing transfers heat to the TGP layer which disperses the heat over the entire implant surface (covered with TGP), thus eliminating the hotspots. See also FIG. 3A. In yet another embodiment, the TGP may be integrated into the housing as a layer within the housing. For example, a titanium or titanium alloy housing may be formed with a layer of TGP inserted into a wall of the housing. This TGP insert would have the same heat dispersal effect as seen above, spreading heat over the entire area that the TGP was inserted and eliminating hotspots. See also FIG. 3B.

Figure 4A:
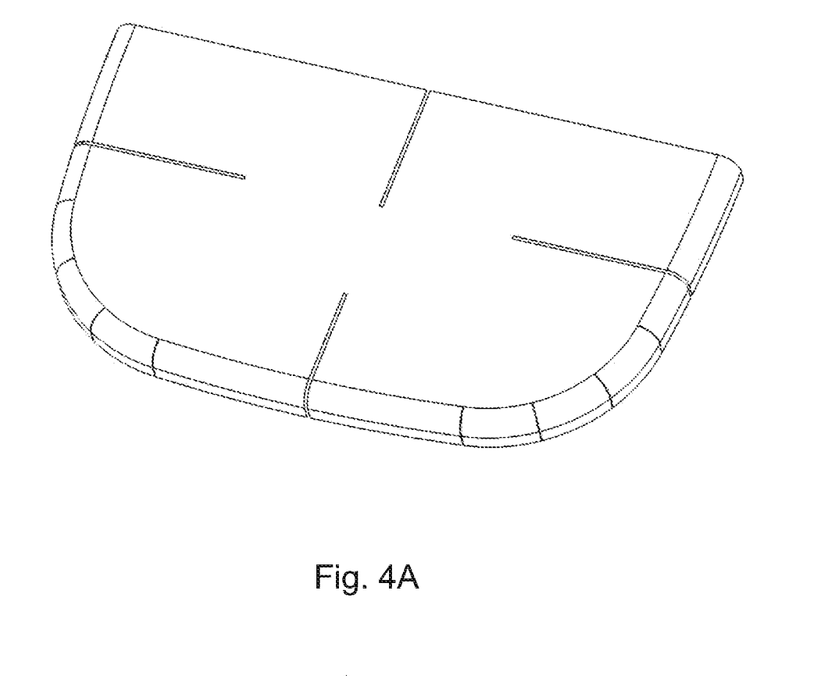
FIG. 4A shows an example heat dissipation sheeting that has been sectioned to reduce eddy currents in the sheeting during inductive charging of the implantable medical device.

FIG. 4A shows a heat dissipation sheeting that may be TGP or highly ordered pyrolytic graphite that has been sectioned to reduce eddy currents in the sheeting during inductive charging of the implantable medical device. The sectioning does not noticeably affect the heat transferring qualities of the sheeting, however, by reducing the eddy currents heating in the sheets reduced during the recharging process. FIG. 4A depicts a thermally conductive sheet of TGP or another thermally conductive material sheet quartered.

Figure 4B:
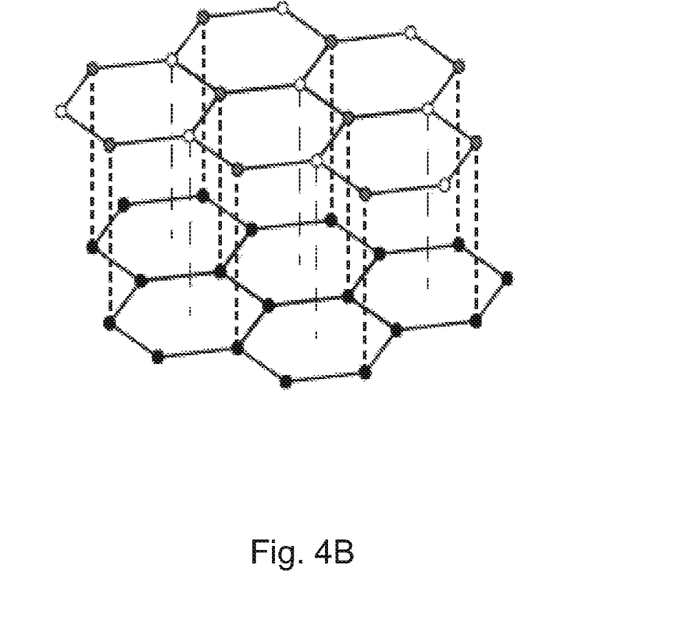
FIG. 4B shows the configuration of a highly ordered pyrolytic graphite that may optionally be used for a heat spreader in the implantable medical device.

The atomic structure or configuration of a highly ordered pyrolytic graphite or TGP is shown in FIG. 4B. Atomic bonds along the a-b layer are ordered and consistent, shown by the connected hexagonal configuration of the carbon atoms. This allows very efficient heat transfer along the direction of the hexagonal carbon bonds (e.g. a-b layer).

In a further embodiment of the thermally conductive material, either copper or aluminum is used to disperse heat throughout the housing of the implant housing. For example, copper and aluminum both have thermal conductivities greater than 200 W/m-K. Thus, copper or aluminum could be disposed between heat generating electrical components and the housing, integrated into the housing, plated on the housing exterior for the purposes of heat transfer, or a combination of these configurations could be utilized.

In some embodiments, the thermally conductive material is a non-metallic material. For example, the thermally conductive material may include different forms of carbon. These forms of carbon may include diamond, highly ordered graphite, highly ordered pyrolytic graphite, and other forms of graphite. The thermally conductive material may also include carbon compounds and/or other elements or compounds that are non-metallic.

In some embodiments, the thermally conductive material may also be a discrete component, in particular where its primary function is thermal transfer. The thermally conductive material may be separate from the electrical circuitry and the housing. The material may be applied to the surface of a housing or an electrical component and still be considered separate from the component. In another example, electrical components made of thermally conductive materials, such as copper in a charging coil, or circuit board substrates provided for support or conductive layers on a circuit board for connecting components, are not considered to be separate from the electrical componentry, even though they may inherently exhibit some heat transfer capabilities. Thus, copper in a charging coil may not be considered a thermally conductive material that is separate from the electrical componentry.

One skilled in the art will realize that copper and aluminum, along with some other metals, provide disadvantages when used in environments with inductive power signals. The electrical resistances of these materials is low in comparison to other materials, therefore eddy currents easily form in these materials. Thus, any benefit from spreading the heat from the internal circuitry, using copper or aluminum, for example, will likely be counteracted by heat created in the copper or aluminum due to eddy currents.

The recharging circuitry of an IMD may be an integral component to an implant's heat management system which includes the use of thermally conductive materials and the appropriate housing. Recharging circuitry is often the greatest heat generator in medical implants and therefore heat management in implants with rechargeable batteries focuses on the recharging system. For example, implants may include temperature sensors for determining if heating is exceeding industry or regulator thresholds, which is 3 degrees Celsius above body temperature. The sensed temperatures may be used to determine if adjustments need to be made to the charging rate.

In the case of implant over-heating, charging parameters may be communicated to an external charger to decrease a magnetic/inductive power field being supplied to the implant, to slow the charging process, thus reducing heating in the charging circuitry of the implant and reducing eddy currents in the implant's housing and the thermally conductive material sheets. In particular, thermally conductive materials may increase the area over which the heat from recharging circuitry components are dissipated and allow for faster recharging. Thus, the design of heat management systems in implants, in this example, are focused on recharging systems for limiting heating and thermally conductive materials to maximize the use of the heat sink, which is the exterior wall of the implant, for example, the implant housing.

Figure 5:
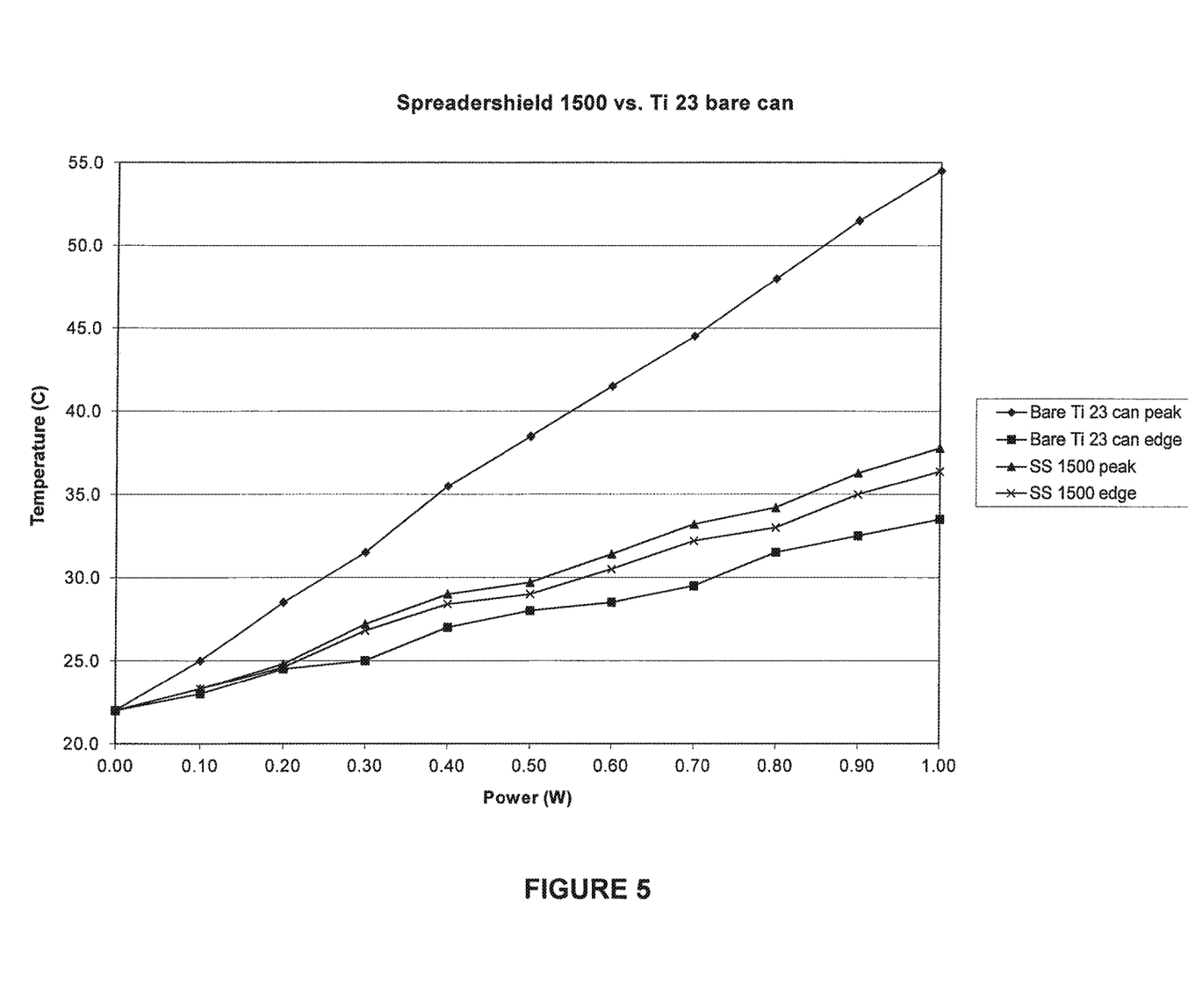
FIG. 5 shows a graph of heat dissipation on two surfaces of the example implantable medical device with and without the heat spreading sheet.

FIG. 5 shows a graph of heat dissipation on two surfaces of the implantable medical device with and without the heat spreading sheet. Bare Ti 23 can is an implantable medical device with a housing manufactured from Grade 23 titanium alloy. Bare signifies that this implant does not have heat spreading capability. In contrast, SS 1500 is the same implant with a heat spreader with a thermal conductivity of greater than 1500 W/m-k. Temperature measurements at the peak with and without the heat spreader show that the use of the heat spreader prevents the accumulation of heat in the implant by spreading the heat over the surface of the housing. Similarly, temperature measurements at the edge with and without the heat shield show similar results.

Figure 6:
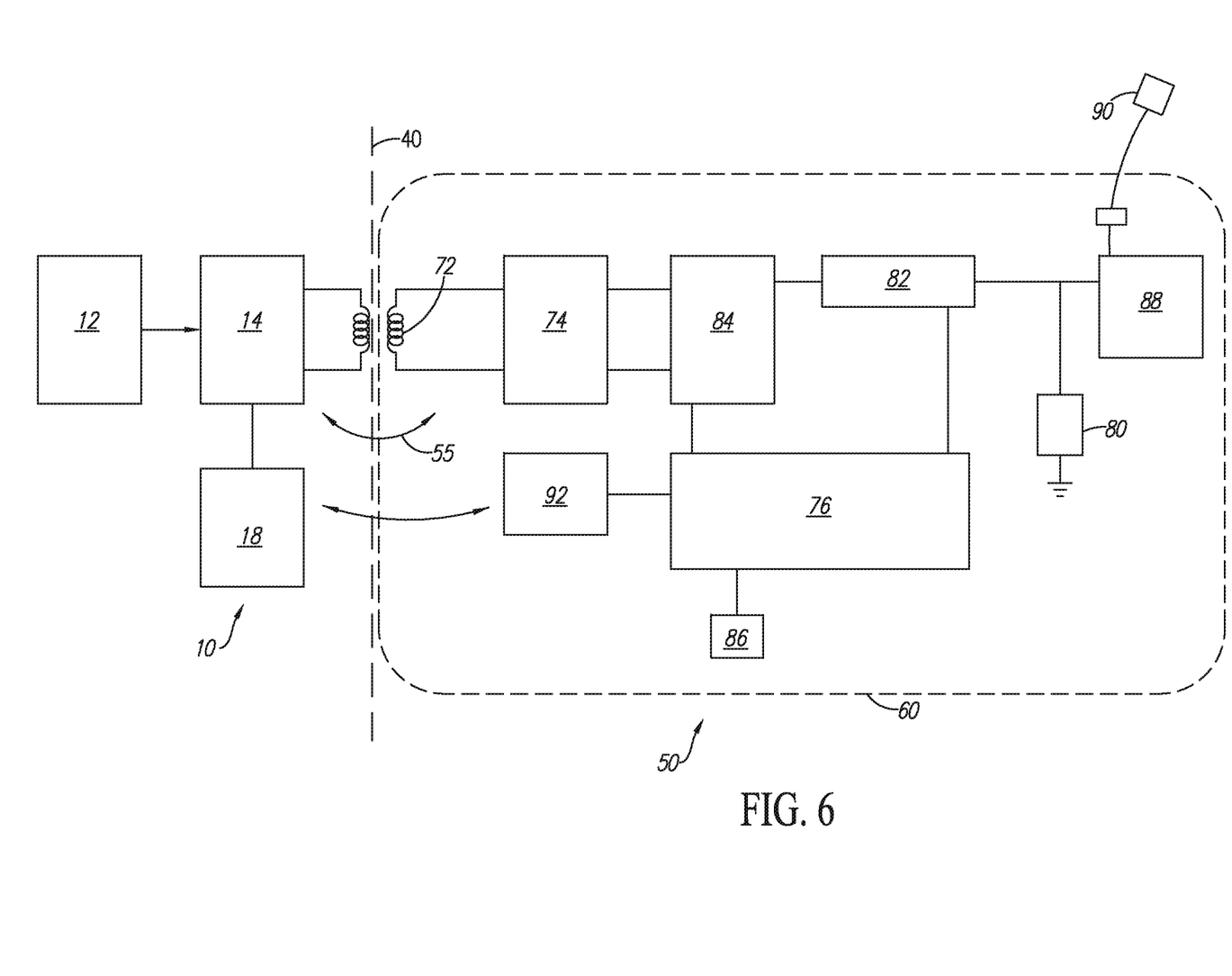
FIG. 6 shows a detailed schematic of another example electrically powered implantable medical device with an external charger.

The implant's recharging circuitry is shown in FIG. 6 in relation to devices and methods for reducing heat in implants during recharging. In one embodiment the electrical circuitry of the IMD further includes therapeutic electrical circuitry (therapeutic controller 88) for providing electrical signals to the therapeutic electrical lead (therapeutic lead 90) and a temperature sensor 86 for determining a surface temperature of the housing 60. Additionally, a recharging circuitry (e.g. charger controller 76, rectifier 74, voltage sensor 82) for recharging a battery 80 that acts as a power source for the therapeutic electrical circuitry. The recharging circuitry also includes an implant coil (implant charger coil 72) that is implanted in a patient for receiving an inductive power field 55 from an external charger 10.

The electrically powered IMD 50, in this example, is recharged by an external charger 10 via an inductive power field 55 transmitted through the skin 40 of a patient. Optionally, the recharging circuitry could be modified to be a powering circuitry for a cochlear implant or other implant that directly powers the implant without a battery.

The external charger 10, which provides the inductive power to the implant's recharging circuitry, includes a power source 12, an oscillator and inductive power controller 14 that controls the power and frequency of the magnetic field (e.g. inductive power field 55) sent from the external coil 16 through the patient's skin to the implant charge coil 72. The external charger 10 may further include a communication and misalignment system 18 for communicating with the implant 50 and determining if the external coil 16 is properly aligned with the implant charge coil 72. Misalignment of these coils may cause an inefficient transfer of the inductive power field 55, and thus increase the heat created on an implant housing 60 via eddy currents. Thus, the communication and misalignment system 18, may be an integral part of the implant's heat management system by maximizing the power received by the implant 50 from the smallest inductive power field 55.

The implantable medical device 50 may optionally include an implant charge coil 72 for receiving the inductive power field 55 from the external charger 10. A rectifier 74, connected to the implant charge coil 72, converts the AC current to a DC current and may further smooth the current with the use of a capacitor (not shown), providing a rectified current for recharging a battery 80 or optionally directly powering a therapeutic controller 88 that provides a therapy for a patient. The therapeutic controller 88 may provide an electrical stimulus to the patient's tissue via therapeutic lead 90, control administration of a medication to the patient, or monitor electrical signals, temperatures, or other patient indicators, for example, via the therapeutic lead 90.

The implantable medical device 50 may further include a charge controller 76 that monitors the voltages of one or more of, the rectified current and the battery 80 via a voltage sensor 82. The charge controller may also monitor a temperature sensor 86, or optionally monitor multiple temperature sensors, to determine the temperature on or near the surface of the implant housing 60 or at other locations within the implant. Temperature sensor 86 may be placed in contact with or proximate to the implant housing 60. Additional temperature sensors may optionally be place throughout the inner chamber of the implant housing 60, the electrical circuitry, and/or the electrical componentry of the IMD that generates heat. The charge controller 76 controls a current regulation and battery protection circuitry 84 which adjusts the current and/or voltage supplied to the battery 80 during recharging. Optionally, the charge controller 76 may control current directly supplied to the therapeutic controller 88.

The charge controller 76 may optionally communicate parameters via implant communicator 92 to misalignment and communication system 18 of the external charger 10 to optimize the amplitude and frequency of the inductive power. In some cases, rapid charging may create excessive heating in the implant housing 60 and/or recharging circuitry (e.g. current regulation and battery protection circuitry 84). The charge controller 76 may detect these temperatures and decrease the charging rate by passing parameters to the external charger to reduce the inductive power.

Additionally, preventative means for reducing heat before it is accumulated (and thus sensed) may be undertaken. The charge controller 76 may optionally reduce heating in the recharging circuitry by measuring the voltage from the rectifier circuit 74, determining adjustment parameters, and communicating these parameters via implant communicator 92 to misalignment and communication system 18 of the external charger 10. An optimized amplitude and frequency of the inductive power 55, provided by the adjustment parameters, may reduce the need for the implant's current regulation to step down voltages from the rectifier circuit 74 using voltage divider circuits (e.g. resistors), thus reducing heat in the recharging circuitry.

Additionally, the implant charge coil 72 may be a substantial generator of heat when receiving inductive power. The charge controller 76 may sense temperature spikes in the coil and communicate, to the external charger 10, adjustments to the amplitude and the frequency of the inductive power signal 55. Thus, communications between the implant's charge controller 76 and the external charger 10 may be an effective component of an implant's heat dissipation system to decrease heat generated in the recharging circuitry. Additionally, placement of thermally conductive materials near heat generating electrical componentry, like the voltage divider of the current regulation and battery protection circuitry 84 and the implant charge coil 72 may contribute to an effective heat dispersion system.

The implant housing 60 in FIG. 6 is shown to include all of the electrical circuitry (minus the therapeutic lead 90). However, in another embodiment certain circuitry may be external to the implant housing 60. It may be understood by one skilled in the art that implant housing 60 may include one inner chamber or two separate inner chambers. Furthermore, housing 60 may actually be two or more housings containing different components of the electrical circuitry. Example, the implant coil 52 may be in one inner chamber separate from the other electrical circuitry.

Forming a housing for the rechargeable implantable medical device out of a titanium alloy (e.g., Ti-6Al-4V ELI (extra-low interstitial) alloy or Grade 23, Ti-3Al-2.5V alloy or Grade 9, etc.), rather than pure titanium, can provide advantages due to the higher electrical resistivity of titanium alloys. The higher electrical resistivity of titanium alloys reduces eddy currents that form in the housing during charging. Eddy currents are generally undesirable because they can heat the housing to unacceptably high temperatures and they reduce charging efficiency. Eddy currents can be controlled by reducing the power transmitted by the charger to the implantable medical device. However, reducing the power increases charging time. Thus, using titanium alloy rather than pure titanium for housings of rechargeable implantable medical devices provides the advantages of decreased surface heating and more efficient and quicker charging of the device. An example of such a housing is disclosed in related U.S. Pat. No. 9,630,231 issued on Apr. 25, 2017 and incorporated herein by reference.

In another embodiment, the material for the housing is also selected for its electrical resistance properties, for the purpose of reducing eddy currents. Alloys of titanium, particularly titanium #9 and #23 have been determined to have high electrical resistance while still being possible to form into an implant housing including an internal chamber that may be hermetically sealed. These materials, in combination with heat spreading materials like TGP, CAPG, other graphite compositions may be combined to form housings and heat spreaders that reduce inductive heating during recharging of the implant's battery.

In another embodiment, the inductive power signal 55 from the external charger 10 passes through, at least, the skin 40 of a patient, the thermally conductive material (shown in FIG. 6), and the housing 60 before reaching the implant coil. The thermally conductive material and a material of the housing may also be selected to have low magnetic permeability to allow the inductive power 55 to pass through the housing 60 and the thermally conductive material to the implant coil without generating substantial eddy currents and heating.

In yet another embodiment, the material of the housing and/or the thermally conductive material is selected to be safely implanted in a human body. In the case of the thermally conductive material being safe to be implanted in the human body, the material could be coated on the exterior of the housing to disperse heat from within the implant. The material of the housing may be selected so that it may be formed to include an inner chamber that is hermetically sealed to the exterior of the housing.

Figure 7:
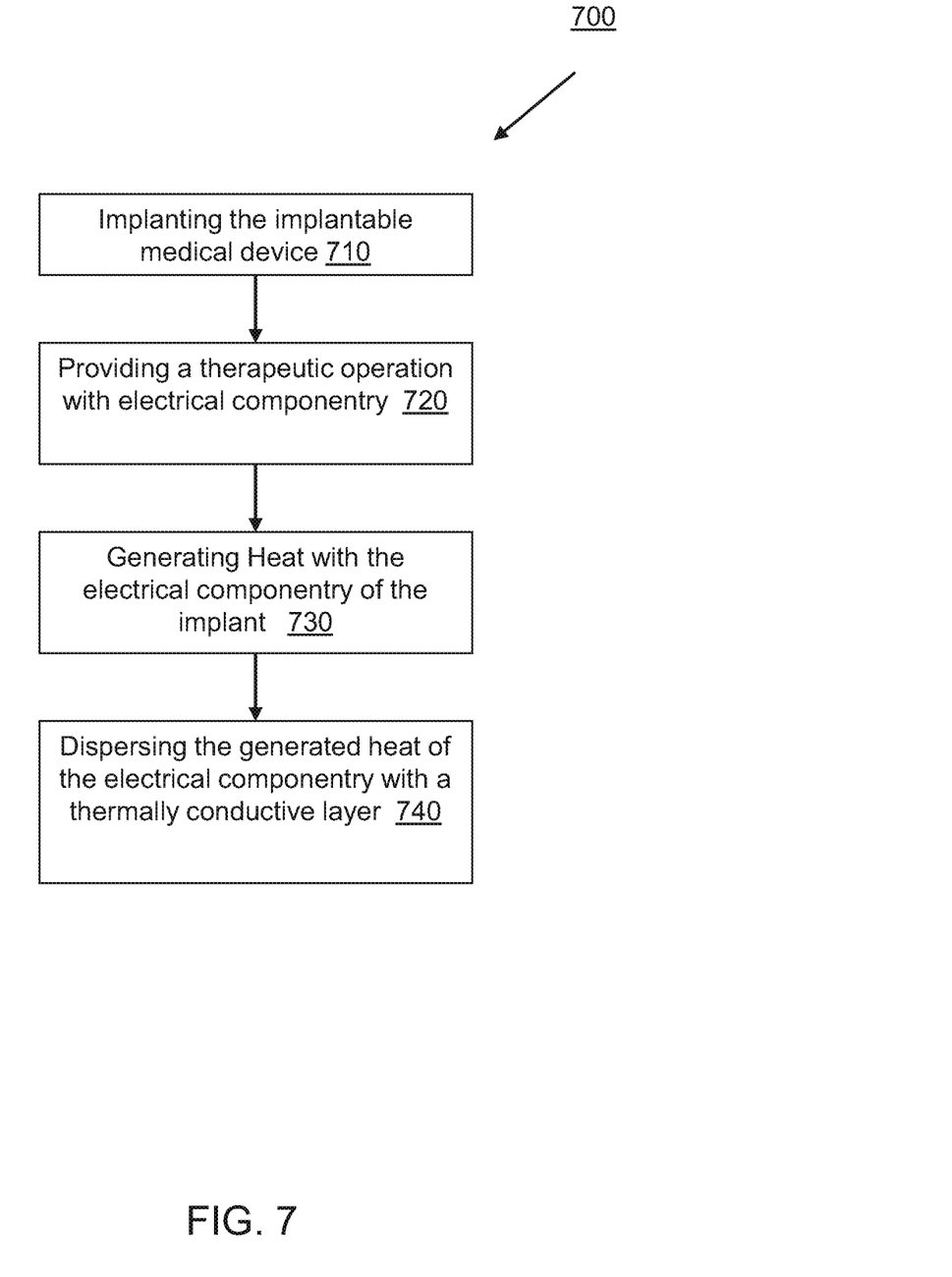
FIG. 7 is a flow chart showing another example embodiment of a method associated with the disclosure.

FIG. 7 shows a flow diagram of example steps for a method 700 for providing a therapy with an implantable medical device. The method 700 optionally includes, implanting the implantable medical device 710 including an electrical componentry. At least some of the electrical componentry associated with the method is located inside a housing of the implantable medical device. The method 700 further includes providing a therapeutic operation with the electrical componentry 720. The therapeutic operation may include providing an electrical stimulus to a patient and the tissue of the patient or reading electrical signals, temperature signals, sensing motion, or taking other readings with the electrical circuitry. The method 700 further includes generating heat with the electrical componentry 730, which may be generated during the inductive recharging of the power supply of the implantable medical device, rapidly discharging the battery during an emergency, providing a therapy, or any other reason that the implant may be causing heating due to operations by the electrical circuitry.

The method 700 may further include dispersing the generated heat of the electrical componentry with a thermally conductive layer 740 from a first portion of the housing that is located in proximity to said generating heat of the electrical componentry to a second portion of the housing that is not located in proximity to said generated heat of the electrical componentry. The thermally conductive layer may be associated with the thermally conductive material of claim 1, TGP, HOPG, or any other heat conductive material, with or without planar differences in thermal conductivity. Optionally, the thermally conductive layer may be one or more of, located within the housing between the housing and said generated heat of the electrical componentry, located within a wall of the housing as an integrated housing component, and located on the exterior of the housing as a coating between the housing and a tissue that surrounds the implantable medical device.

The method 700 for providing a therapy may optionally include, dispersing heat generated by the electrical componentry with the thermally conductive layer. In particular, dispersing heat with a first plane thermal conductivity of greater than 1000 W/m-K while a second plane thermal conductivity of less than 10 W/m-K. TGP may be one of the materials that satisfies these thermal conductive qualities.

The heat generated in the electrical componentry of method 700 may be cause, at least in part, by the recharging of an implant battery of the implantable medical device. Recharging the implant battery may include: receiving inductive power with an implant coil, wherein the inductive power is provided by an external coil of an external charger, converting the inductive power with at least a portion of the electrical componentry to a charging current, and providing the charging current to the implant battery.

Figure 8:
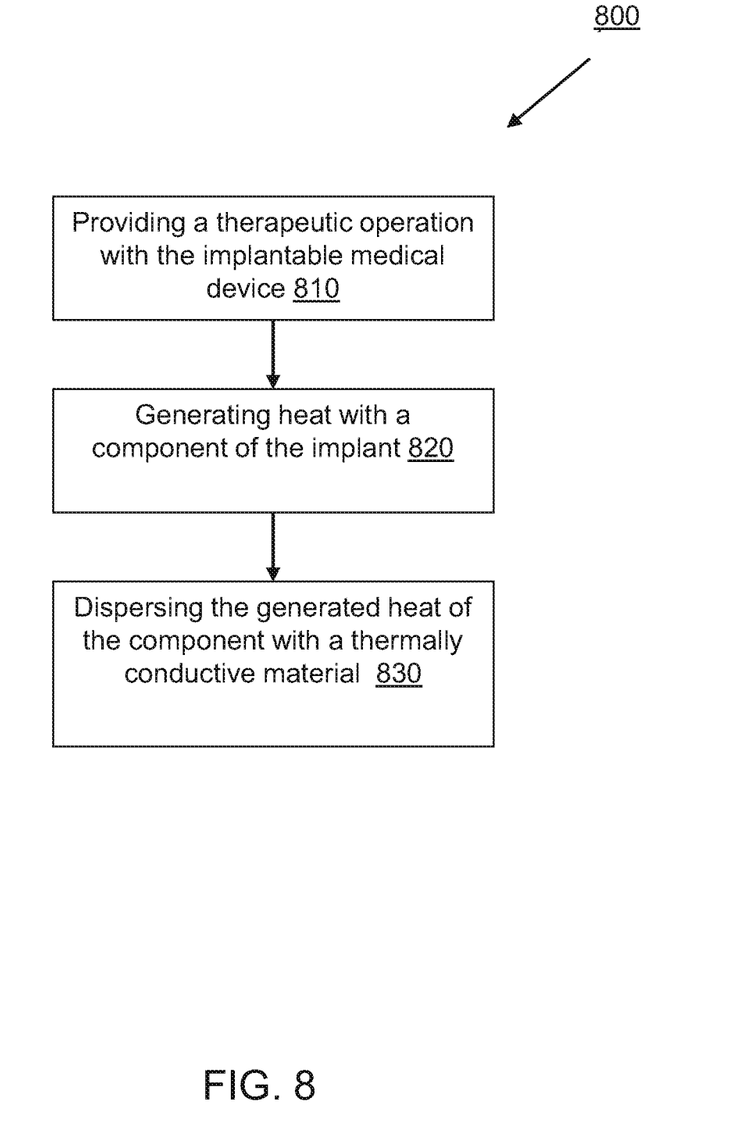
FIG. 8 is a flow chart showing another example embodiment of a method associated with the disclosure.

FIG. 8 shows a flow diagram of example steps for a method 800 for transferring heat in an implantable medical device including, providing a therapeutic operation with the implantable medical device 810. The method 800 further includes, generating heat with a component of the implant 820 and dispersing heat generated by the component with a thermally conductive material 830 from a first portion of the implantable medical device located in proximity to said heat generating component to a second portion of the implantable medical device that is not located in proximity to said generated heat of the component.

Figure 9:
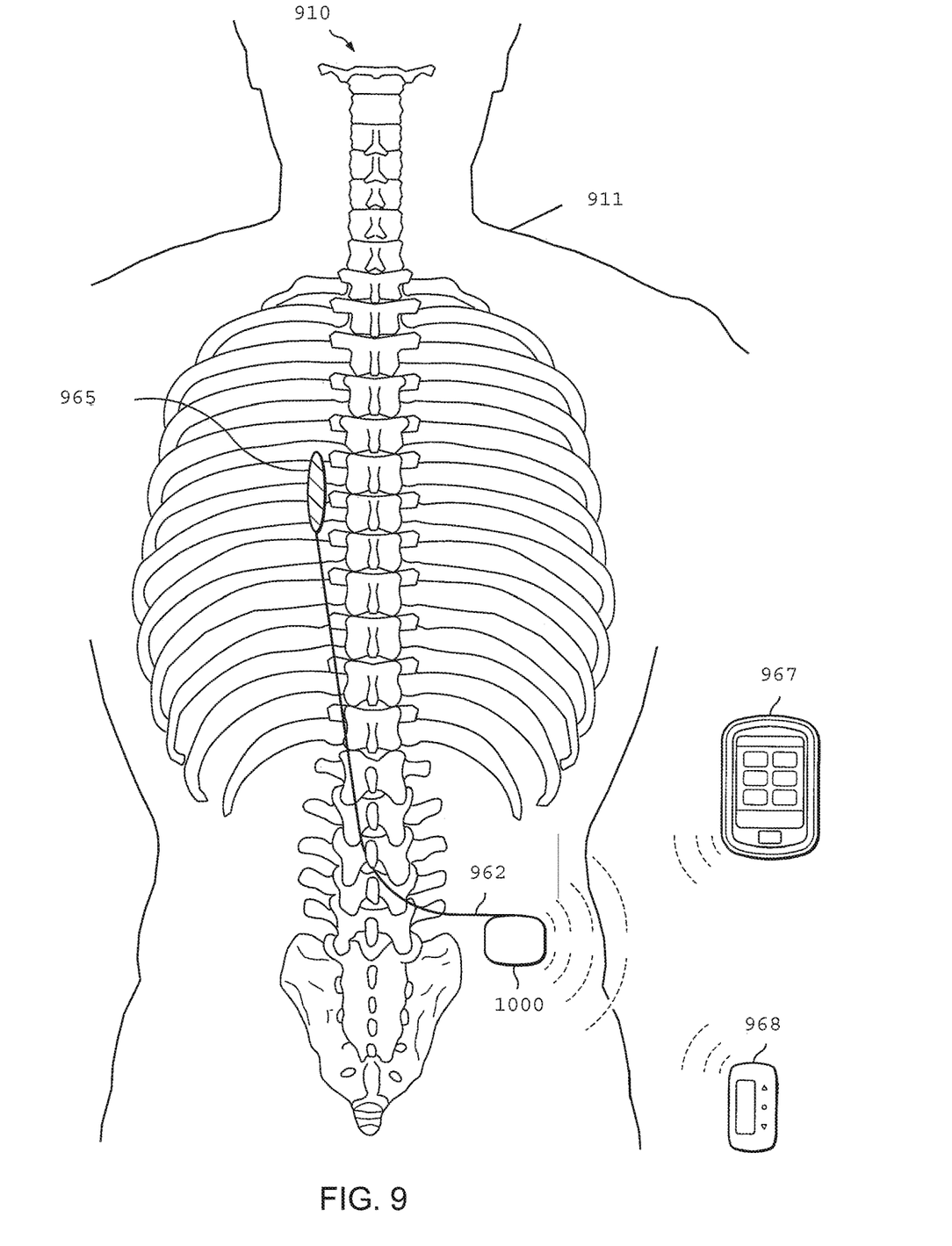
FIG. 9 shows an example implantable device in a patient.

FIG. 9 shows an example application of an implanted medical device for providing spinal stimulation to a patient 911. In that figure, the implanted medical device is an implantable pulse generator (IPG) 1000 shown implanted in a patient for providing pulse stimulation of the patient's spinal cord (in the spine 910) for the purpose of providing pain therapy. The IPG 1000 can be comprised of an internal power supply (that may include a rechargeable battery), a controller, pulse generation electronics, protection/conditioning circuits, and a contact assembly for connecting to an electrode array. The IPG 1000 can be supported by an external power supply (such as for charging the battery of the internal power supply), and a clinician programmer 967 and a user controller 968. Also shown is the human spine 910 in proximity with the stimulation Electrodes 965 that are attached to the IPG 1000 via electrode leads 962.

The leads and electrodes may be positioned anywhere along the spine to deliver the intended therapeutic effects of spinal cord electrical stimulation in the desired region of the spine. The distal end of the lead with its accompanying electrodes may be located along the epidural space and adjacent to a desired portion of the spinal cord using well-established and known techniques for implanting and positioning SCS leads and electrodes, and the IPG 1000 may be programmed using a clinician programmer 967 or other type of programmer 968 (such as a patient controller), as desired. The electrode leads 965 can be connected to the IPG via a contact assembly as described in this application.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:

1. An implantable medical device, comprising:
electrical circuitry that includes a heat generating component;
a sheet disposed adjacent to the heat generating component, wherein the sheet contains a thermally conductive material configured to spread heat generated by the heat generating component; and
a housing within which the electrical circuitry and the sheet are located, wherein the sheet conforms to interior contours of the housing.

2. The implantable medical device of claim 1, wherein the sheet is a first sheet, and wherein the implantable medical device further comprises a second sheet that contains the thermally conductive material, and wherein the first sheet and the second sheet are located on opposite sides of the heat generating component.

3. The implantable medical device of claim 1, wherein the thermally conductive material includes a non-metallic material.

4. The implantable medical device of claim 1, wherein the thermally conductive material includes pyrolytic graphite.

5. The implantable medical device of claim 4, wherein the pyrolytic graphite includes carbon atoms arranged into a connected hexagonal configuration.

6. The implantable medical device of claim 1, wherein:
the sheet has a first thermal conductivity across one or more directions defined by a planar surface of the sheet;
the sheet has a second thermal conductivity in a direction perpendicular the planar surface of the sheet; and
the first thermal conductivity is at least an order of magnitude greater than the second thermal conductivity.

7. The implantable medical device of claim 6, wherein the sheet is oriented such that the planar surface faces the heat generating component.

8. The implantable medical device of claim 7, wherein the sheet includes an electrically insulating layer disposed on the planar surface.

9. The implantable medical device of claim 1, wherein the thermally conductive material is a first thermally conductive material, and wherein the implantable medical device further comprises a second thermally conductive material applied on an exterior surface of the housing.

10. The implantable medical device of claim 9, wherein the second thermally conductive material is further applied on an interior surface of the housing.

11. The implantable medical device of claim 9, wherein the first thermally conductive material and the second thermally conductive material have different material compositions.

12. The implantable medical device of claim 1, wherein a layer of the thermally conductive material is inserted into a wall of the housing.

13. A medical system, comprising:
an electronic programmer configured to receive instructions for programming an implantable medical device; and
the implantable medical device, wherein the implantable medical device includes:
electrical circuitry that includes a heat generating component;
a sheet disposed adjacent to the heat generating component, wherein the sheet contains a non-metallic thermally conductive material configured to disperse heat generated by the heat generating component; and
a housing within which the electrical circuitry and the sheet are located, wherein the sheet is located between the housing and the heat generating component;
wherein:
a wall of the housing has a thermally conductive layer inserted therein, the thermally conductive layer containing a same type of thermally conductive material as the sheet; or
a thermally conductive coating is applied on an interior surface or an exterior surface of the housing, the thermally conductive coating containing a same type of thermally conductive material as the sheet.

14. The medical system of claim 13, wherein:
the sheet is a first sheet;
the implantable medical device further comprises a second sheet that contains the thermally conductive material;
the first sheet and the second sheet are located on opposite sides of the heat generating component; and
the first sheet and the second sheet each includes an electrically insulating layer facing the heat generating component.

15. The medical system of claim 13, wherein the thermally conductive material includes pyrolytic graphite having carbon atoms arranged into a connected hexagonal configuration.

16. The medical system of claim 13, wherein:
the sheet has a planar layer facing the heat generating component; and
the sheet has a greater thermal conductivity across the planar layer than through the planar layer.

17. An implantable medical device, comprising:
electrical circuitry that includes a heat generating component;
a thermally conductive sheet having a planar surface facing the heat generating component, wherein the thermally conductive sheet has a first thermal conductivity across the planar surface and a second thermal conductivity in a direction perpendicular to the planar surface, the first thermal conductivity being at least an order of magnitude greater than the second thermal conductivity, and wherein an electrically insulating layer is disposed on the planar surface, thereby providing electrical insulation between the electrical circuitry and the thermally conductive sheet; and
a housing within which the electrical circuitry and the thermally conductive sheet are located, wherein the sheet is located between the housing and the heat generating component.

18. The implantable medical device of claim 17, wherein the thermally conductive sheet is a first thermally conductive sheet, and wherein the implantable medical device further comprises a second thermally conductive sheet, wherein the first thermally conductive sheet and the second thermally conductive sheet are located on opposite sides of the heat generating component.

19. The implantable medical device of claim 17, wherein the thermally conductive sheet includes a non-metallic material.

20. The implantable medical device of claim 17, wherein a thermally conductive material is coated on an interior surface of the housing.

* * * * *